United States Patent
Greco et al.

(10) Patent No.: US 9,980,888 B2
(45) Date of Patent: May 29, 2018

(54) CLEANSING COMPOSITION WITH A HYDROPHILIC PHASE AND A LIPOPHILIC PHASE COMPRISING A COMBINATION OF ESTERS

(71) Applicant: JOHNSON & JOHNSON CONSUMER INC., Skillman, NJ (US)

(72) Inventors: Joseph James Greco, South Plainfield, NJ (US); Claudia Kaminski, Milford, NJ (US); Prithwiraj Maitra, Hillsborough, NJ (US); Snehal M. Shah, Hillsborough, NJ (US); Christopher Paul Ferrara, South Amboy, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days. days.

(21) Appl. No.: 15/521,347

(22) PCT Filed: Mar. 18, 2015

(86) PCT No.: PCT/US2015/021136
§ 371 (c)(1),
(2) Date: Apr. 24, 2017

(87) PCT Pub. No.: WO2016/073024
PCT Pub. Date: May 12, 2016

(65) Prior Publication Data
US 2017/0304170 A1  Oct. 26, 2017

Related U.S. Application Data

(60) Provisional application No. 62/074,691, filed on Nov. 4, 2014.

(51) Int. Cl.
*A61K 8/37* (2006.01)
*A61Q 1/14* (2006.01)
(Continued)

(52) U.S. Cl.
CPC .............. *A61K 8/37* (2013.01); *A47K 7/02* (2013.01); *A47K 10/32* (2013.01); *A61K 8/0208* (2013.01);
(Continued)

(58) Field of Classification Search
None
See application file for complete search history.

(56) References Cited

U.S. PATENT DOCUMENTS 6,063,397 A    5/2000  Fowler et al.
6,762,158 B2   7/2004  Lukenbach et al.
(Continued)

FOREIGN PATENT DOCUMENTS

DE    102007024465 A1    11/2008
FR        2984725 A1     6/2013
(Continued)

OTHER PUBLICATIONS

Ross, John and Miles, Gilbert, "An Apparatus for Comparison of Foaming Properties of Soaps and Detergents", Oil & Soap (1941) p. 99-102.
(Continued)

*Primary Examiner* — Robert A Wax
*Assistant Examiner* — Melissa S Mercier

(57) ABSTRACT

A personal care composition including at least one dry emollient and one oily emollient, where the personal care composition is free of silicone or silicone containing materials.

18 Claims, 5 Drawing Sheets

(51) Int. Cl.
*A61Q 19/00* (2006.01)
*A61K 8/02* (2006.01)
*A47K 10/32* (2006.01)
*A47K 7/02* (2006.01)
*A61K 8/33* (2006.01)

(52) U.S. Cl.
CPC ............... *A61K 8/33* (2013.01); *A61Q 1/14* (2013.01); *A61Q 19/00* (2013.01); *A47K 2010/3266* (2013.01); *A61K 2800/34* (2013.01)

(56) References Cited

U.S. PATENT DOCUMENTS

| | | |
|---|---|---|
| 7,074,747 B1 | 7/2006 | Lukenbach et al. |
| 7,262,158 B1 | 8/2007 | Lukenbach et al. |
| 9,333,155 B1 | 5/2016 | Greco et al. |
| 2010/0068162 A1 | 3/2010 | Greenberg |

FOREIGN PATENT DOCUMENTS

| | | | |
|---|---|---|---|
| WO | WO1997/026860 A1 | 7/1997 | |
| WO | WO2010/019939 A1 | 2/2010 | |
| WO | WO-2010019939 A1 * | 2/2010 | ............... A61K 8/37 |

OTHER PUBLICATIONS

International search report dated May 26, 2015, for corresponding international application PCT/US2015/021136.

* cited by examiner

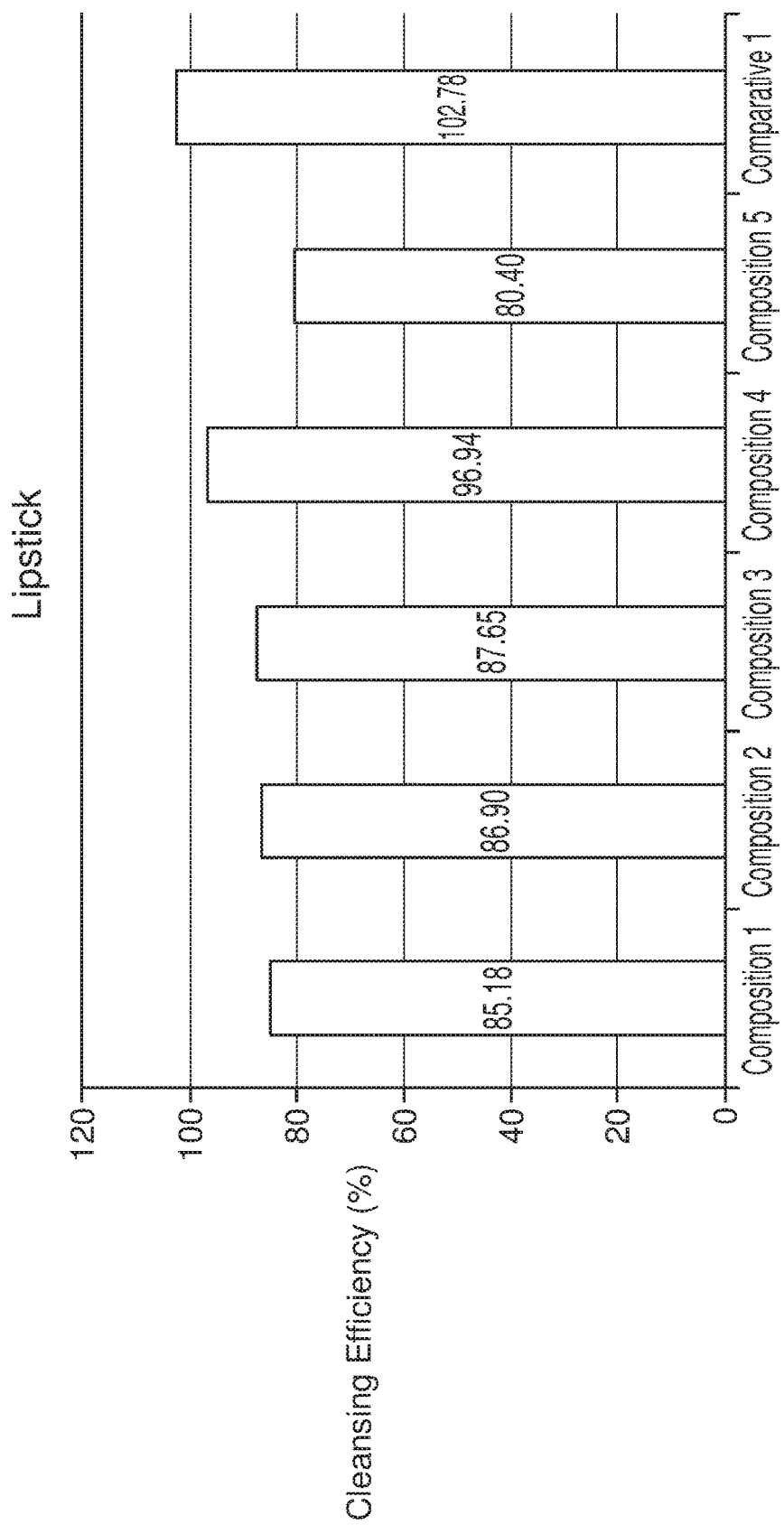

CLEANSING COMPOSITION WITH A HYDROPHILIC PHASE AND A LIPOPHILIC PHASE COMPRISING A COMBINATION OF ESTERS

CROSS-REFERENCE TO RELATED APPLICATIONS

This application is the national stage filing under 35 USC 371 of international application PCT/US2015/021136 filed on Mar. 18, 2015, which claims priority to U.S. provisional application 62/074,691 filed on Nov. 4, 2014, the complete disclosure of which is hereby incorporated herein by reference for all purposes.

FIELD OF THE INVENTION

The present invention relates to cleansing compositions, particularly cleaners for the skin and for make-up removal applications. Specifically, the personal care compositions are useful for providing non-irritating cleansing to users, and therefore are suitable for individuals with sensitive skin and eyes. The compositions provide suitable cleaning of at least three types of cosmetics, while leaving the skin feeling clean and without a greasy residue. The compositions are sufficiently free of silicone or silicone-containing materials.

BACKGROUND

Because of the wide variety of skin, hair and nail problems faced by consumers, consumers have long sought personal care products which can cleanse the skin, or deliver and/or deposit benefit agents that alleviate such problems. A facial cleanser should desirably provide a suitable cleansing efficiency for removal of foundation, mascara and lipstick. It is important, however, to avoid sacrificing the ability of products to adequately cleanse the skin in favor of reducing irritation to a user. Many delivery systems sacrifice aesthetics and cleaning ability in order to achieve stability and reduced irritation. This is particularly true when such products are to be used on sensitive areas, such as on the face, and even more particularly, in the very sensitive regions surrounding the eyes. When high amounts of particular cleansers, such as dry emollients, are used as the sole cleansing component, there is a risk of irritation of the eyes and skin, particularly in the face. Some cleansers have attempted to provide suitable non-irritation through the use of compositions including silicones. The present invention seeks to avoid using silicones while still providing a non-irritating or at least reduced irritating cleanser while achieving superior cleansing efficacy.

Accordingly, it would be desirable to create such a composition that is capable of cleaning the skin of a user adequately, where the composition has a low degree of ocular and skin irritation and avoids the use of silicones.

SUMMARY

In some aspects, the present invention includes a cleansing composition, a method of making or using a cleansing composition, and kits including a cleansing composition, where the cleansing composition includes a combination of a dry emollient and an oily emollient. The cleansing composition is desirably free of silicone or silicone-containing components. The cleansing composition may be provided or used as a wipe, where the wipe includes a sufficient amount of the cleansing composition contained therein.

The invention may be a personal care composition including: (a) from about 8 weight percent to about 12 weight percent, based upon the total weight of the composition, of at least one dry emollient and one oily emollient; (b) from about 85 weight percent to about 90 weight percent, based upon the total weight of the composition, of water; where the personal care composition is free of silicone or silicone containing materials.

In some aspects, there is included a method of cleaning the skin of a user without irritating skin, including the step of: (a) applying a personal care composition to the skin of a user, the composition including: (i) from about 8 weight percent to about 12 weight percent, based upon the total weight of the composition, of at least one dry emollient and one oily emollient; (ii) from about 85 weight percent to about 90 weight percent, based upon the total weight of the composition, of water; where the personal care composition is free of silicone or silicone containing materials; and (b) one of rinsing the composition off the skin, leaving the composition to dry on the skin, or wiping the composition off the skin.

The invention may further include a cleansing kit or method of using a cleansing kit, the kit including a resealable package and a plurality of wipes, where each wipe contains a sufficient amount of a personal care composition contained therewithin.

BRIEF DESCRIPTION OF THE FIGURES

FIG. 5 is a chart summarizing the test data for ten cycles in Example 5.

DETAILED DESCRIPTION

Figure 1:
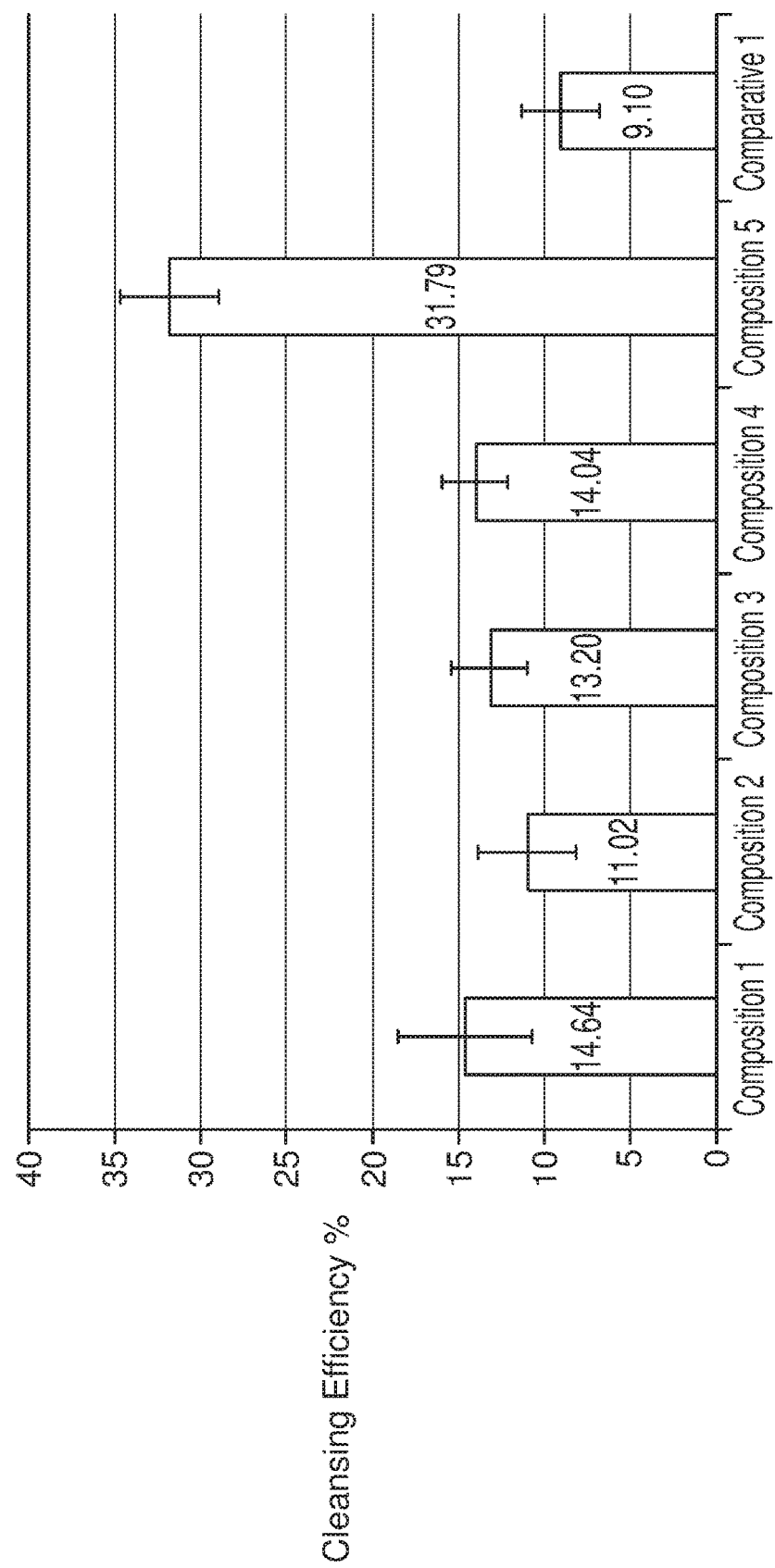
FIG. 1 is a chart summarizing the test data of Example 3.

The present invention provides compositions and materials that deliver optimal properties. As used herein, the term "optimal" includes comparable or improved cleansing efficacy when compared to known cleansers. Optimal does not necessarily mean 100% cleansing efficiency, but rather is a suitable efficiency to remove various cosmetics from the face. Other benefits provided by the cleaning compositions of the present invention may include one or more of the following: aesthetics, reduced greasiness, low irritation of skin and eyes, achieving shorter drying time and lower cost, reducing the amount of cleansing agents in the composition, and enabling the cleaning compositions to be free of silicone.

As used herein, the term "percent" shall refer to the weight percent. As also used herein, the term "water dispersible component" shall mean a material that produces a uniform, clear or hazy, mixture when combined with at least a weight equivalent of water. The term "benefit agent" used herein includes any active ingredient that is to be delivered into and/or onto the skin, hair or nail at a desired location, including but not limited to agents such as a cosmetic agent or a pharmaceutical agent. By "cosmetic agent," it is meant any ingredient that is appropriate for cosmetically treating, providing nutrients to, and/or conditioning the hair, nail, and/or skin via topical application. By "pharmaceutical agent," it is mean any drug that is appropriate for topical use.

As used herein, "medicament agents" include those agents capable of promoting recovery from injury and illness.

Generally, the present invention includes cleaning compositions including a combination of water, thickener(s), humectant(s), emollient(s), preservative(s), fragrance(s), excipient(s), extract(s), and sodium hydroxide. Various combinations of the foregoing components are useful in the present invention. The compositions may be useful in liquid or gel form, to be applied by hand, or in combination with a wipe, sheet or sponge, so as to be applied by an applicator device.

The cleansing compositions useful in the present invention may be formulated comprising a combination of at least two emollients As used herein, "emollients" refer to materials used for cleansing the skin, hair, and eye lashes, the prevention or relief of dryness, or for the protection of the skin. Examples of emollients include, but are not limited to, hydrophobic compounds such as vegetable oils, mineral oils (e.g., petrolatum), fatty esters (e.g., isopropyl palmitate, c12-c15 alkyl benzoate) including those fatty esters of glycerol and the like.

It is desirable to include a combination of a "dry" emollient and an oily emollient. Dry emollients and oily emollients will be understood through a description of the material and examples suitable for such emollient. For example, dicaprylyl carbonate is considered a "dry" emollient, in that it dries and is removed from the skin of a user fairly rapidly. One particular oily emollient is heptyl undecylenate, which is more oily and is more difficult to remove from the skin of a user, but provides suitable cleansing. Although each emollient can provide suitable cleansing when used in high amounts (e.g., about 8-12%) by itself, it is particularly desired to use a combination of emollients to adequately clean but also protect the skin. When a dry emollient is used by itself in amounts of about 8-12%, there is a risk of irritation of the skin and eyes, particularly over time as the emollient penetrates the skin. When an oily emollient is used by itself in amounts of about 8-12%, it leaves a greasy/oily residue on the skin, which must be removed with further washing. Thus, in the present invention, it is useful to avoid cleansing compositions include only a dry emollient or only an oily emollient. In an embodiment of the present invention, it may be desired to include a combination of a first dry emollient (e.g., dicaprylyl carbonate) and a first oily emollient (e.g., heptyl undecylenate). It may also be desired to include these two components in a combined amount of about 6-10 percent by weight of the total composition, more desirably about 8% by weight of the total composition. As will be described in more detail below, when a combination of dry and oily emollients is used, the ratio of dry:oily emollient is from about 6:1 to about 1:1, and more desirably about 3:1 to about 1:1. Thus, for example, a cleansing composition may include about 6% dry emollient and about 2% oily emollient.

In another embodiment of the present invention, it may be desired to include a dry emollient and an oily emollient in combination with humectants and an emulsifying agent, such as a glyceride or triglyceride. For example, a combination may include caprylic/capric triglyceride, dicaprylyl carbonate, propanediol and heptyl undecylenate. Other components that may be useful in the present invention also include mineral oil, lanolin, vegetable oils, isostearyl isostearate, isostearyl palmitate, isostearyl isononanoate, glyceryl laurate, hexanoates, including pentaerythrityl tetraethylhexanoate and cetyl ethylhexanoate, methyl gluceth-10, methyl gluceth-20 chitosan, and mixtures thereof. The composition is desirably free of silicone or silicone-containing components.

As noted above, the relative amounts and ratios of certain components are useful in providing the desired product. For example, it is useful to include a weight ratio of a dry emollient (e.g., dicaprylyl carbonate) to an oily emollient (e.g., heptyl undecylenate) of about 3:1. The compositions may include water in an amount of about 80 to about 95 percent of the composition, and more desirably between about 85-92 percent water by weight of the total composition. Water may be present in an amount sufficient as required. The inventive compositions may include thickeners, emollients, humectants, emulsifying agents, preservatives, extracts, excipients, fragrances, neutralizers, and stabilizers in an amount of from about 20 to about 5 percent, and more desirably about 15 to about 8 percent by weight of the composition. Thickeners may be present in an amount of about 0.1 to about 0.5 percent by weight of the composition. Emollients may be present in an amount of from about 5 to about 15 percent by weight of the composition, and more specifically about 6 to about 12 percent by weight of the composition. Humectants may be present in an amount of from about 1 to about 5 percent by weight of the composition. Surfactants may be present in an amount of from about 0.5 to about 3 percent by weight of the composition. Preservatives may be present in an amount of about 0.5 to about 2 percent by weight of the composition. Fragrances may be present in an amount of about 0.1 to about 0.5 percent by weight of the composition. Extracts may be present in an amount of about 0.05 to about 0.1 percent by weight of the composition. If used, a neutralizer such as sodium hydroxide may be present in minor amounts, such as about 0.01 to about 0.05 percent by weight of the composition. Optional benefit agents may be present in any desired amount.

As noted above, the personal care composition includes a particular combination of dry and oily emollients. If only two emollients are used in combination, it is useful to include a carbonate, such as dicaprylyl carbonate as the dry emollient, and heptyl undecylenate as the oily emollient. Compositions may additionally include one or both of a glyceride, such as caprylic/capric triglyceride and a humectant, such as an aliphatic diol, such as propanediol.

A useful emollient useful in the present invention includes dry emollients. Any suitable dry emollients may be used, including, for example, a carbonate ester, an ester of carbonic acid, having the structure:

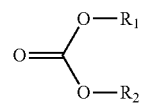

where $R_1$ and $R_2$ may be the same or may be different, and are $C_6$ to $C_{30}$ alkyl groups. A preferred carbonate ester is dicapryl carbonate, also known as dioctylcarbonate, dicaprylyl carbonate, or carbonic acid, dioctyl ester. Dicaprylyl carbonate is commercially available under the trade name Cetiol CC, available from BASF. Dicaprylyl carbonate has the following structure:

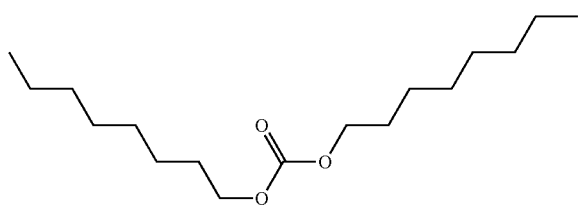 [SMILES: CCCCCCCCOC(=O)OCCCCCCCC]

Other useful carbonate esters include, but not limited to cetyl carbonate, cetearyl carbonate, stearyl carbonate, $C_{12}$-$C_{15}$ alkyl carbonate and the like. The dry emollient is particularly useful in the present inventive compositions. In some aspects, the dry emollient is present in an amount of equal to or greater than other emollients in the composition.

A second useful emollient of the present invention is an oily emollient, as described above, which may include heptyl undecylenate (also known as 10-undecenoic acid heptyl ester). Heptyl undecylenate is commercially available under the trade name LexFeel, available from Inolex. Oily emollients are useful due to their ability to remain on the skin surface or in the stratum corneum to act as a lubricant, to reduce flaking, and to improve the skin's appearance, as well as to remove oily compositions and cosmetics from the skin. Other useful oily emollients include esters such as, but not limited to tridecyl neopentanoate, isostearyl palmitate, cetyl ricinoleate, cetyl octanoate, isononyl isononanoate, butyl stearate, octyldodecyl soyate, tridecyl erucate, and octyldodecyl erucate/eicosil erucate, diisopropyl adipate, dioctyl sebacate, dioctyl succinate, dioctyl maleate, diisostearyl adipate, and diethyl sebacate.

The cleaning composition may additionally include an emulsifying agent. One example of an emulsifying agent is a glyceride or a triglyceride, an ester derived from glycerol and three fatty acids, having the structure:

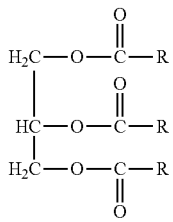

Wherein R is linear or branched, saturated or unsaturated, C6-C30 alkyl moieties, such as decyl, undecyl, dodecyl (lauryl), tridecyl, tetradecyl (myristyl), pentadecyl, hexadecyl (cetyl, palmityl), heptadecyl, heptadecenyl, hepta-8-decenyl, hepta-8,11-decenyl, octadecyl (stearyl), nonadecyl, eicosanyl, henicosen-12-yl, henicosanyl, docosanyl (behenyl), and the like. Certain preferred hydrophobic moieties include heptadecyl, heptadecenyl, hepta-8-decenyl, hepta-8,11-decenyl and the like. Preferably, the triglyceride is a caprylic/capric acid triglyceride also known as caprylic/capric acid triglyceride; decanoic acid, ester with 1,2,3-propanetriol octanoate; decanoic acid, ester with 1,2,3-prpanetriol octanoate; decanonic acid, ester with 1,2,3-propanetriol octanoate; glycerol calrylate caprinate; glycerol caprylate caprinate; octanoic/decanoic acid triglyceride; ester with 1,2,3-propanetriol octanoate decanoic acid; ester with 1,2,3-propanetriol octanoate decanoic acid; or ester with 1,2,3-propanetriol octanoate decanonic acid EWG.

Caprylic/capric triglyceride may be made from fractionated coconut oil, meaning a specific density of the coconut oil is extracted. This oil has a very long shelf life and is a suitable carrier oil for essential oils, and plant and flower extracts and may be useful to help create a barrier on the skin which helps skin to retain moisture and protect the skin. Caprylic/capric triglyceride is available under the trade names Tegosoft CT/Crodamol GTCC, commercially available from Evonik Industries. Other useful triglycerides include, but not limited to esterification products formed from glycerol and fatty acids such as adipic acid, succinic acid, sebacic acid, maleic acid, lauric acid, myristic acid, palmitic acid, margaric acid and any combination thereof.

Another useful component in the present invention is a humectant, such as an aliphatic diol. One suitable such diol is propanediol (or 1,2, propane diol). Suitable aliphatic diols include those commercially available under the trade name Zemea, available from DuPont. Other useful aliphatic diols include, but are not limited to butanediol, pentanediol and hexanediol, and derivatives thereof.

As explained above, it is useful to include a combination of at least a first dry emollient and a first oily emollient. If the composition includes only about 8-10% of a dry emollient, the composition has a risk of irritation to the skin, particularly when the skin is the face and near the eyes. Further, over time, the dry emollient begins to penetrate the skin and risk damaging healthy components of the skin. If the composition includes only about 8-10% of an oily emollient, the composition is difficult to remove from the skin and requires further washing to remove the composition after it is applied. Use of compositions including only oily emollients as the cleansing agent leaves the user's skin feeling greasy and requires further cleaning.

The various emollients may be provided in any desired combination, and preferably a dry emollient and an oily emollient are included in a ratio of about 3 to about 1 (by weight). Thus, in one example, dicaprylyl carbonate may be present in an amount of about 6 percent by weight of the composition and heptyl undecylenate may be present in an amount of about 2 percent by weight of the composition (or any other amounts within the 3:1 ratio). In some embodiments, the dry emollient may be present in an amount approximately equal to the amount of the oily emollient (e.g., dicaprylyl carbonate in an amount of 4% and heptyl undecylenate in an amount of 4%). In embodiments including a humectant, it may be included in an amount less than the dicaprylyl carbonate, and in some embodiments, the humectant may be present in an amount approximately equal to the heptyl undecylenate. If included, a triglyceride may be present in an amount less than dicaprylyl carbonate, and may be present in an amount less than heptyl undecylenate.

The compositions described herein are useful in removing various cosmetic products from the skin of users, and in particular, are useful in removing mascara, foundation and lipstick efficiently and without remaining residue. Mascara is a notoriously difficult cosmetic material to remove from skin, as it deposits high levels of film formers and includes a relatively high level of hydrophobic materials. Further, mascara includes a high level of carbon dark pigments, giving it a dark color. In addition, since mascara is typically applied on the eyes or eyelashes, cleaning requires a gentle, low pressure and non-planar application. Lipstick presents its own difficulties in removal, as it includes anhydrous materials, such as waxes, which may be difficult to remove. Foundation provides some difficulty as well, as it is typically an emulsion and may include silicones, which cause it to remain on the skin. Cosmetics today are geared towards a "24-hour" use, where the cosmetic remains on the skin of the user for an extended period of time. These "long-lasting" cosmetics have a high transfer resistance, making them difficult to remove.

To provide a material that effectively and sufficiently removes enough of these three cosmetic materials is particularly desired. Further, it is desired to provide a composition that does not leave an oily or greasy residue on the surface of the skin, since such oily cleansers may be difficult to remove and leave the user with an unclean feeling. In addition, it is important that the cleansing composition provide low or no irritation to the skin, particularly the eyes. For this reason, it is useful to include a combination of a dry emollient and an oily emollient. Although compositions including only dry emollients may be suitable as cleaners, they risk irritation to the user. Similarly, compositions including only oily emollients are useful in cleaning the cosmetic, they leave an oily and greasy residue and therefore are less desired in the present compositions.

Another embodiment of the present invention is directed to a personal care system comprising, consisting, or consisting essentially of, based upon the total weight of the personal care system, a) at least about 5 percent or at least about 10 percent of the combination of emollients in the personal care composition described above; b) from about 80 percent to about 95 percent, and preferably from about 85 percent to about 92 percent of water; c) from about 0.1 percent to 5 percent, preferably, from about 0.5 percent to about 1.5 percent of a polymeric emulsifier, a thickener, or mixture thereof; d) from about 0.001 to about 0.05 percent a neutralizer; and optionally e) from about 0.001 percent to about 5 percent of a benefit agent. In one embodiment, the personal care system may comprise, based upon the total weight of the personal care system, from about 0.1 to about 5 percent, and preferably from about 0.5 percent to 1.5 percent of a polymeric emulsifier and/or from about 0.01 percent to about 2 percent, and preferably from about 0.01 percent to about 0.5 percent of a thickener. More preferably, the personal care system contains, based upon the total weight of the personal care system, non-water components from about 5 percent to about 20 percent of the personal care composition.

The personal care system may be in the form of an oil-in-water emulsion, a water-in-oil emulsion, or a dispersion.

In addition to the emollients described above, the personal care system may include polymeric emulsifiers and/or thickeners. Emulsifiers that may be useful include the emulsifying agents described above, such as glycerides or triglycerides, including, for example, caprylic/capric triglyceride. As used herein, the term "polymeric emulsifier" shall mean those compounds capable of emulsifying systems whereby the polymeric emulsifiers have a molecular weight of at least about 5000, and preferably are block copolymers having a hydrophilic portion and a hydrophobic portion. When used at amounts effective for emulsifying the personal care system, the polymeric emulsifiers surprisingly do not cause significant eye sting, i.e., when the emulsifier-containing composition was used by 80 consumers in the eye area, no more than about 5% of such users expressed discomfort around the eye area. Examples of suitable polymeric emulsifiers nonexclusively include polyethylene glycol-30 dipolyhydroxystearate available from Uniqema under the tradename, "Arlacel P-135;" dimethicone copolyol, which is available from Goldschmidt Chemical Corporation under the tradename, "Abil EM 90"; substituted acrylates such as those available from The Goodrich Corporation under the tradename, "Pemulen"; and mixtures thereof.

Examples of suitable hydrophilic thickeners nonexclusively include carbomers available from B. F. Goodrich under the tradename, "Carbopol ETD 2020", acrylate copolymers and acrylate crosspolymers, hydroxyethylcellulose modified with cetyl ether groups available from Hercules under the tradename, "Natrosol Plus", polyvinylmethyl ether/maleic anhydride (PVM/MA) decadiene crosspolymer available from International Specialty Products under the tradename, "Stabileze QM," and copolymers and mixtures thereof, with carbomers being preferred. Examples of suitable acrylate copolymers nonexclusively include acrylate copolymers available from Rohm & Haas under the tradename, "Aculyn 33," acrylates/aminoacrylates copolymer available from National Starch & Chemical Company under the tradename, "Structure Plus," acrylates/steareth-20 itaconate copolymer available from National Starch & Chemical Company under the tradename, "Structure 2001," acrylates/ceteth-20 itaconate copolymer available from National Starch & Chemical Company under the tradename, "Structure 3001," acrylates/steareth-20 methacrylate copolymer available from Rohm & Haas under the tradename, "Aculyn 22," and copolymers and mixtures thereof.

Preservatives that may be useful in the present invention include, for example, ethylhexylglycerin, dehydroacetic acid, benzoic acid, phenoxyethanol, polyaminopropyl biguanide, chlorphenesin, PEG-4 Laurate, iodopropynyl butylcarbamate, and mixtures thereof.

Fragrances may be used in the present invention as desired. Suitable fragrances include those commonly known and used in cleansers, including non-irritating fragrances. Some fragrances that may be useful in the present invention include, for example, diva mod 4 RY-007326 and orchid dew, among other suitable non-irritating fragrances.

Extracts useful in the present invention include, for example, glycerin, hydrolyzed caesalpinia spinosa gum and protein extracts, such as soybean protein extract. The invention may further include any desired excipient or combination of excipients.

The personal care system of the present invention may also optionally contain a stability enhancer for the purpose of enhancing the stability of the benefit agent and/or the aesthetics of the personal care system. Generally, the stability enhancer is selected from a nonionic emulsifier, an essentially non-foaming surfactant or mixtures thereof. Examples of suitable nonionic emulsifiers include isoceteth-20, oleth-2, mixture of PEG-40 hydrogenated castor oil and trideceth-9 available from Dragoco Inc. under the tradename, "Dragoco Solubilizer 2/014160," Poloxamer 184, laureth-4, sorbitan trioleate, polyoxyethylene-(2) oleyl ether, sorbitan stearate, cetearyl glucoside, glyceryl oleate, trideceth-9, polyethylene glycol-40 hydrogenated castor oil, and mixtures thereof.

Examples of suitable essentially non-foaming surfactants include non-foaming nonionic surfactants such as sucrose esters, e.g., sucrose cocoate, sucrose stearate and mixtures thereof, with sucrose cocoate being preferred, which is commercially available under the trade name Tegosoft LSE, available from Evonik Industries. By "essentially non-foaming," it is meant that the surfactant, when used with the composition of the present invention, has a column height of less than about 20 mm as determined by the Ross-Miles Foam Generation Test. See 18 (I.) Oil & Soap 99-102 (1941)["Ross-Miles Test"), which is incorporated by reference herein. The personal care composition and the personal care system may either be rinseable with water or may be wiped-off. Preferably, the essentially, non-foaming surfactants are used in embodiments wherein the personal care system or the personal care composition is rinseable with water. An example of a suitable stability enhancer include a mixture of sorbitan stearate and sucrose cocoate available from Uniqema under the tradename, "Arlatone 2121."

When desired, the personal care system may contain, based upon the total weight of the personal care system, less than about 6%, and preferably 5%, of the stability enhancers for cream formulations and may include no more than about 2%, and preferably no more than 1% of the stability enhancers in thin lotion/milk formulations.

The personal care system and personal care composition may also optionally contain a foaming surfactant. The foaming surfactant may be non-ionic, cationic, amphoteric, or anionic; nonionic surfactants are preferred. By "foaming," it is meant that the surfactant, when used with the composition of the present invention, has a column height of foam greater than about 20 mm as determined by the Ross-Miles Test. As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. Examples of suitable and preferred surfactants may be found in International Patent Application Number WO97/01196, which is incorporated by reference in its entirety herein.

The personal care system and personal care composition may further optionally contain one or more benefit agents or pharmaceutically-acceptable salts thereof. As used herein, the term "benefit agent" includes any active ingredient that is to be delivered into and/or onto the skin, hair or nail at a desired location, such as a cosmetic agent or a pharmaceutical agent. By "cosmetic agent," it is meant any ingredient that is appropriate for cosmetically treating, providing nutrients to, and/or conditioning the hair, nail, and/or skin via topical application. By "pharmaceutical agent," it is mean any drug that is either hydrophobic or hydrophilic in nature and appropriate for topical use. As used herein "medicament agents" include those agents capable of promoting recovery from injury and illness.

The benefit agents useful herein may be categorized by their therapeutic benefit or their postulated mode of action. However, it is to be understood that the benefit agents useful herein may, in some circumstances, provide more than one therapeutic benefit or operate via greater than one mode of action. Therefore, the particular classifications provided herein are made for the sake of convenience and are not intended to limit the benefit agents to the particular application(s) listed. In addition, the compounds, which are identified below as being suitable for use as benefit agents, may be used in an amount over and above the amount that they may be used for other purposes in the personal care composition or personal care system.

Examples of suitable benefit agents include, but are not limited to, depigmentation agents; reflectants; detangling/wet combing agents; film forming polymers; humectants; amino acids and their derivatives; antimicrobial agents; allergy inhibitors; anti-acne agents; anti-aging agents; anti-wrinkling agents, antiseptics; analgesics; antitussives; antipruritics; local anesthetics; anti-hair loss agents; hair growth promoting agents; hair growth inhibitor agents, antihistamines such as *Mandragora Vernalis, Tanacetum Parthenium* and the like; antiinfectives such as *Acacia Catechu, Aloe Barbadensis, Convallaria Majalis, Echinacea, Eucalyptus, Mentha Piperita, Rosa Canina, Sassafras Albidum,* and the like; inflammation inhibitors; anti-emetics; anticholinergics; vasoconstrictors; vasodilators; wound healing promoters; peptides, polypeptides and proteins; deodorants and antiperspirants; medicament agents; skin emollients and skin moisturizers; skin firming agents, hair conditioners; hair softeners; hair moisturizers; vitamins; tanning agents; skin lightening agents; antifungals such as *Centaurea Cyanus, Kalmia Latifolia* and antifungals for foot preparations; depilating agents; shaving preparations; external analgesics; perfumes; counterirritants; hemorrhoidals; insecticides; poison ivy products; poison oak products; burn products; antidiaper rash agents; prickly heat agents; make-up preparations; vitamins; amino acids and their derivatives; herbal extracts; retinoids; flavenoids; sensates; anti-oxidants; skin conditioners; hair lighteners; chelating agents; cell turnover enhancers; coloring agents; pigments; sunscreens, those active ingredients disclosed in U.S. Pat. No. 6,063,397, which is incorporated herein by reference, anti-edema agents, collagen enhancers, and mixtures thereof.

Examples of suitable anti-edema agents nonexclusively include bisabolol natural, synthetic bisabolol, and mixtures thereof.

Examples of suitable vasoconstrictors nonexclusively include horse chestnut extract, prickly ash, and mixtures thereof.

Examples of suitable anti-inflammatory agents nonexclusively include benoxaprofen, centella asiatica, bisabolol, feverfew (whole), feverfew (parthenolide free), green tea extract, green tea concentrate, hydrogen peroxide, lycopene including "Lyc-o-Pen" available from LycoRed Natural Products Industries, Ltd., oat oil, chamomile, and mixtures thereof.

Examples of collagen enhancers nonexclusively include vitamin A, vitamin C, and mixtures thereof.

Examples of suitable skin firming agent nonexclusively include dimethylaminoethanol ("DMAE").

Examples of suitable antipruritics and skin protectants nonexclusively include oatmeal, betaglucan, feverfew, soy and derivatives thereof, bicarbonate of soda, colloidal oatmeal, surfactant based colloidal oatmeal cleanser, *Anagallis Arvensis, Oenothera Biennis, Verbena Officinalis,* and the like. These antipruritics may be used in an amount, based upon the total weight of the personal care composition, from about 0.01 percent to about 40 percent, and preferably from about 1 percent to about 5 percent.

As used herein, colloidal oatmeal means the powder resulting from the grinding and further processing of whole oat grain meeting United States Standards for Number 1 or Number 2 oats. The colloidal oatmeal has a particle size distribution as follows: not more than 3 percent of the total particles exceed 150 micrometers in size and not more than 20 percent of the total particles exceed 75 micrometers in size. Examples of suitable colloidal oatmeals include, but are not limited to, "Tech-O" available from the Beacon Corporation and colloidal oatmeals available from Quaker.

Examples of suitable reflectants nonexclusively include mica, alumina, calcium silicate, glycol dioleate, glycol distearate, silica, sodium magnesium fluorosilicate, and mixtures thereof.

Suitable detangling/wet combing agents nonexclusively include polyquatemium-10, hydroxypropyltrimonium guar, dioleoylamidoethyl hydroxyethylmonium methosulfate, di-(soyoylethyl) hydroxyethylmonium methosulfate, hydroxyethyl behenamidopropyl dimonium chloride, olealkonium chloride, polyquatemium-47, stearalkonium chloride, tricetylmonium chloride, and mixtures thereof.

Suitable film forming polymers include those that, upon drying, produce a substantially continuous coating or film on the hair, skin, or nails. Nonexclusive examples of suitable film forming polymers include acrylamidopropyl trimonium chloride/acrylamide copolymer; corn starch/acrylamide/sodium acrylate copolymer; polyquatemium-10; polyquatemium-47; polyvinylmethylether/maleic anhydride copolymer; styrene/acrylates copolymers; and mixtures thereof.

As noted above, humectants may be useful in the invention, including aliphatic diols. Other commercially available humectants which are capable of providing moisturization and conditioning properties to the personal care composition are suitable for use in the present invention. The humectant is preferably present in an amount of from about 0 percent to about 10 percent, more preferably from about 0.5 percent to about 5 percent, and most preferably from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, pentylene glycol, dipropylene glycol, and mixtures thereof; 2) polyalkylene glycol of the formula I.:

$$HO\text{---}(R''O)_b\text{---}H \qquad (I).$$

wherein R'' is an alkylene group having from about 2 to about 4 carbon atoms and b is an integer of from about 1 to about 10, such as PEG 4; 3) polyethylene glycol ether of methyl glucose of formula II.:

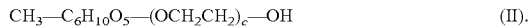

$$CH_3\text{---}C_6H_{10}O_5\text{---}(OCH_2CH_2)_c\text{---}OH \qquad (II).$$

wherein c is an integer from about 5 to about 25;

4) urea; 5) fructose; 6) glucose; 7) honey; 8) lactic acid; 9) maltose; 10) sodium glucuronate; and 11) mixtures thereof.

Suitable amino acid agents include amino acids derived from the hydrolysis of various proteins as well as the salts, esters, and acyl derivatives thereof. Examples of such amino acid agents nonexclusively include amphoteric amino acids such as alkylamido alkylamines, i.e. stearyl acetyl glutamate, capryloyl silk amino acid, capryloyl collagen amino acids; capryloyl keratin amino acids; capryloyl pea amino acids; cocodimonium hydroxypropyl silk amino acids; corn gluten amino acids; cysteine; glutamic acid; glycine; hair keratin amino acids; amino acids such as aspartic acid, threonine, serine, glutamic acid, proline, glycine, alanine, cystine, valine, methionine, isoleucine, leucine, tyrosine, phenylalanine, cysteic acid, lysine, histidine, arginine, cysteine, tryptophan, citrulline; lysine; silk amino acids, wheat amino acids; and mixtures thereof.

Suitable proteins include those polymers that have a long chain, i.e. at least about 10 carbon atoms, and a high molecular weight, i.e. at least about 1000, and are formed by self-condensation of amino acids. Nonexclusive examples of such proteins include collagen, deoxyribonuclease, iodized corn protein; milk protein; protease; serum protein; silk; sweet almond protein; wheat germ protein; wheat protein; alpha and beta helix of keratin proteins; hair proteins, such as intermediate filament proteins, high-sulfur proteins, ultra-high-sulfur proteins, intermediate filament-associated proteins, high-tyrosine proteins, high-glycine tyrosine proteins, tricohyalin, and mixtures thereof.

Examples of suitable vitamins nonexclusively include vitamin B complex; including thiamine, nicotinic acid, biotin, pantothenic acid, choline, riboflavin, vitamin B6, vitamin B12, pyridoxine, inositol, carnitine; vitamins A, C, D, E, K and their derivatives such as vitamin A palmitate and pro-vitamins, e.g. (i.e. panthenol (pro vitamin B5) and panthenol triacetate) and mixtures thereof.

Examples of suitable antibacterial agents nonexclusively include bacitracin, erythromycin, neomycin, tetracycline, chlortetracycline, benzethonium chloride, phenol, and mixtures thereof.

Examples of suitable skin emollients and skin moisturizers nonexclusively include mineral oil, lanolin, vegetable oils, isostearyl isostearate, glyceryl laurate, methyl gluceth-10, methyl gluceth-20 chitosan, and mixtures thereof.

Examples of suitable hair conditioners nonexclusively include quaternized compounds such as behenamidopropyl PG-dimonium chloride, tricetylmonium chloride, dihydrogenated tallowamidoethyl hydroxyethylmonium methosulfate, and mixtures thereof as well as lipophilic compounds like cetyl alcohol, stearyl alcohol, hydrogenated polydecene, and mixtures thereof.

Examples of suitable hair moisturizers nonexclusively include panthenyl ethyl ether, phytantriol, and mixtures thereof.

Examples of sunscreen agents nonexclusively include benzophenones, bornelone, butyl paba, cinnamidopropyl trimethyl ammonium chloride, disodium distyrylbiphenyl disulfonate, paba, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, Padimate O, red petrolatum, and mixtures thereof.

An example of a suitable tanning agent nonexclusively includes dihydroxyacetone.

Examples of skin lightening agents nonexclusively include hydroquinone, catechol and its derivatives, ascorbic acid and its derivatives, and mixtures thereof.

Examples of suitable insecticides (including insect repellents, anti-scabies and anti-lice treatments) nonexclusively include permethrin, pyrethrin, piperonyl butoxide, imidacloprid, N,N-diethyl toluamide, which refers to the material containing predominantly the meta isomer, i.e., N,N-diethyl-m-toluamide, which is also known as DEET; compounds of the formula III.

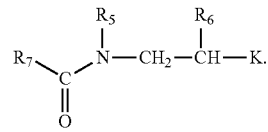

wherein

R$_5$ is a branched or unbranched alkyl group having about 1 to about 6 carbon atoms;

R$_5$ is H, methyl or ethyl;

R$_7$ is a branched or unbranched alkyl or alkoxy group having from about 1 to about 8 carbon atoms; and K is a —CN or a —COOR$_8$ group, wherein R$_8$ is a branched or unbranched alkyl group having from about 1 to about 6 carbon atoms, natural or synthetic pyrethroids, whereby the natural pyrethroids are contained in pyrethrum, the extract of the ground flowers of *Chrysanthemum cinerariaefolium* or *C*

*coccineum*; and mixtures thereof. Within the structure of Formula III. are ethyl 3-(N-butylacetamido)propionate, wherein $R_7$ is a $CH_3$ group, $R_5$ is an n-butyl group, $R_6$ is H, K is $COOR_8$ and $R_8$ is ethyl, which is available commercially from Merck KGaA of Darmstadt, Germany under the name, "Insect Repellent 3535."

An example of an anti fungal for foot preparations nonexclusively includes tolnaftate.

Examples of suitable depilating agents nonexclusively include calcium thioglycolate, magnesium thioglycolate, potassium thioglycolate, strontium thioglycolate, and mixtures thereof.

Examples of suitable external analgesics and local anesthetics nonexclusively include benzocaine, dibucaine, benzyl alcohol, camphor, capsaicin, capsicum, capsicum oleoresin, juniper tar, menthol, methyl nicotinate, methyl salicylate, phenol, resorcinol, turpentine oil, and mixtures thereof.

Examples of suitable antiperspirants and deodorants nonexclusively include aluminium chlorohydrates, aluminium zirconium chlorohydrates, and mixtures thereof.

Examples of suitable counterirritants nonexclusively include camphor, menthol, methyl salicylate, peppermint and clove oils, ichtammol, and mixtures thereof.

An example of a suitable inflammation inhibitor nonexclusively includes hydrocortisone, *Fragaria Vesca*, *Matricaria Chamomilla*, and *Salvia Officinalis*.

Examples of suitable hemorrhoidal products nonexclusively include the anesthetics such as benzocaine, pramoxine hydrochloride, and mixtures thereof; antiseptics such as benzethonium chloride; astringents such as zinc oxide, bismuth subgallate, balsam Peru, and mixtures thereof; skin protectants such as cod liver oil, vegetable oil, and mixtures thereof.

Benefit agents nonexclusively include DMAE, soy and derivatives thereof, colloidal oatmeal, sulfonated shale oil, olive leaf, elubiol, 6-(1-piperidinyl)-2,4-pyrimidinediamine-3-oxide, finasteride, ketoconazole, salicylic acid, zinc pyrithione, coal tar, benzoyl peroxide, selenium sulfide, hydrocortisone, sulfur, menthol, pramoxine hydrochloride, tricetylmonium chloride, polyquaternium 10, panthenol, panthenol triacetate, vitamin A and derivatives thereof, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, retinol, erthromycin, tretinoin, and mixtures thereof.

One type of benefit agent includes those therapeutic components that are effective in the treatment of dandruff, seborrheic dermatitis, and psoriasis as well as the symptoms associated therewith. Examples of such suitable benefits agents nonexclusively include zinc pyrithione, anthralin, shale oil and derivatives thereof such as sulfonated shale oil, selenium sulfide, sulfur; salicylic acid; coal tar; povidoneiodine, imidazoles such as ketoconazole, dichlorophenyl imidazolodioxalan, which is commercially available from Janssen Pharmaceutica, N. V., under the tradename, "Elubiol", clotrimazole, itraconazole, miconazole, climbazole, tioconazole, sulconazole, butoconazole, fluconazole, miconazole nitrate and any possible stereo isomers and derivatives thereof; piroctone olamine (Octopirox); selenium sulfide; ciclopirox olamine; anti-psoriasis agents such as vitamin D analogs, e.g. calcipotriol, calcitriol, and tacaleitrol; vitamin A analogs such as esters of vitamin A, e.g. vitamin A palmitate, retinoids, retinols, and retinoic acid; corticosteroids such as hydrocortisone, clobetasone, butyrate, clobetasol propionate and mixtures thereof.

The amount of benefit agent to be combined with the personal care composition or the emulsion may vary depending upon, for example, the ability of the benefit agent to penetrate through the skin, hair or nail, the specific benefit agent chosen, the particular benefit desired, the sensitivity of the user to the benefit agent, the health condition, age, and skin, hair, and/or nail condition of the user, and the like. In sum, the benefit agent is used in a "safe and effective amount," which is an amount that is high enough to deliver a desired skin, hair or nail benefit or to modify a certain condition to be treated, but is low enough to avoid serious side effects, at a reasonable risk to benefit ratio within the scope of sound medical judgment. If included, a benefit agent may be present in the personal care composition or personal care system in an amount, based upon the total weight of the composition/system, from about 0.01 percent to about 5.0 percent, and preferably from about 0.01 percent to about 2.0 percent, and more preferably from about 0.01 percent to about 1.0 percent.

Optionally, commercially available detergent thickeners that are capable of imparting the appropriate viscosity to conditioning compositions are suitable for use in this invention. If used, the detergent thickeners should be present in the compositions in an amount sufficient to raise the Brookfield viscosity of the composition to a value of between about 500 to about 10,000 centipoise. Examples of suitable detergent thickeners nonexclusively include: mono or diesters of polyethylene glycol of formula IV.

$$HO-(CH_2CH_2O)_zH \qquad (IV).$$

wherein z is an integer from about 3 to about 200; fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. More specifically, suitable detergent thickeners nonexclusively include behenalkonium chloride; cetyl alcohol, quaternium-46, hydroxyethyl cellulose, cocodimonium chloride, polyquaternium-6, polyquaternium-7, quaternium-18, PEG-18 glycerol oleate/cocoate, a mixture of acrylates/steareth-50 acrylate copolymer, laureth-3 and propylene glycol, which is commercially available from Goldschmidt under the tradename "Antil 208," a mixture of cocamidopropylbetaine and glyceryl laurate which is commercially available from Goldschmidt under the tradename, "Antil HS60," a mixture of propylene glycol, PEG 55, and propylene glycol oleate, which is commercially available from Goldschmidt under the tradename, "Antil 414 liquid," and mixtures thereof. Preferred detergent thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

The above described personal care composition and personal care system may be prepared by combining the desired components in a suitable container and mixing them under ambient conditions in any conventional mixing means well known in the art, such as a mechanically stirred propeller, paddle, and the like. The composition may be provided in a container in liquid or cream form, whereby it may be applied to the skin by a user by hand, or the composition may be embedded or soaked into a plurality of sheets or wipes, whereby the composition may be applied to the skin by wiping the sheet, wipe, or other device.

Since the composition is to be applied to the face and is desirably used to remove cosmetic materials, it is most preferred that the composition be soaked into a sheet or a wipe and provided to the user in this form. The user then removes the soaked wipe from a suitable air-tight package, and applies it directly to the skin. Thus, a system or package may include a plurality of wipes in a resealable package, where each wipe has been soaked in or otherwise contains a cleansing composition of the present invention. The wipes are desirably disposable and include degradable components, rendering them environmentally friendly and sound.

In another embodiment of the personal care system of the present invention wherein a polymeric emulsifier such as, for example, polyethylene glycol-30 dipolyhydroxystearate (hereinafter "PEG 30") or dimethicone copolyol, are used and water is used as the vehicle, an oil-in-water emulsion may be produced. Although both the PEG 30 and dimethicone copolyol are marketed for use in formulating water-in-oil compositions, it has now been found that oil-in-water emulsions may be created due to the unique processing steps and conditions employed herein. When a thickening agent, preferably a hydrophilic thickening agent, is neutralized in the hydrophilic phase of the present invention comprising a polymeric emulsifier prior to adding the lipophilic phase of the present invention thereto, the resulting emulsion is in the form of a water-in-oil emulsion. Conversely, when a thickening agent, preferably a hydrophilic thickening agent, is neutralized in the hydrophilic phase of the present invention comprising a polymeric emulsifier after the lipophilic phase of the present invention is added to the hydrophilic phase, the resulting emulsion is in the form of an oil-in-water emulsion.

Personal care systems of the present invention that are emulsions may contain, based upon the total weight of the emulsion, from about 0.01 percent to about 2 percent, and preferably from about 0.01 percent to about 0.5 percent of hydrophilic thickeners if used. Suitable neutralizers include any known bases, such as sodium hydroxide, or acids, such as lactic acid, that are capable of neutralizing the hydrophilic thickening agent, in either the hydrophilic phase (if a water-in-oil emulsion is desired) or a mixture of both the hydrophilic phase and the lipophilic phase (if an oil-in-water emulsion is desired) of the present invention to a pH of about 5 to about 7 under ambient temperature. In one embodiment, hydrophilic thickeners including acrylates/aminoacrylates copolymer, acrylates/steareth-20 itaconate copolymer, acrylates/ceteth-20 itaconate copolymer, are preferably neutralized with an acid, such as lactic acid. Hydrophilic thickeners including carbomers, modified hydroxyethylcellulose, polyvinylacetate/maleic anhydride (PVA/MA) decadiene crosspolymer, and acrylates/steareth-20 methacrylate copolymer, are preferably neutralized with a base, such as sodium hydroxide (20%).

In one embodiment, the hydrophilic phase may be comprised of one or more of the following components: water, thickener, stability enhancer, nonfoaming surfactant, and water dispersible component, and the lipophilic phase may be comprised of one or more of the following components: ester, and polymeric emulsifier.

It has been found that the personal care compositions and personal care systems of the present invention possess good aesthetic properties without causing any significant irritation to the skin or ocular discomfort to the user and are particularly suitable for use on the area surrounding the eye. It is well-known in the art that most emulsifiers having a relatively low molecular weight are irritating regardless of their hydrophilic lipophilic balance ("HLB") value. However, it has been found that when the personal care system of the present invention is produced using the particular emollients set forth herein, the resulting composition is gentle and possesses a low degree of ocular and skin irritation. The combination of dry and oily emollients gives a suitable cleansing composition that can clean at least three categories of cosmetics (mascara, foundation, and lipstick) while avoiding irritation as well as a greasy feel to the user. The present invention provides the aforementioned substantially non-irritating cleaning composition in the absence of silicone or silicone containing materials.

The present invention includes not only the personal care composition described above, but also includes a method of using the personal care composition described above. The method includes applying an effective amount of the composition to the skin, including facial skin and near ocular skin, and cleansing the skin with the composition. The composition may be applied to the skin by hand or through use of an applicator, such as a sheet, wet wipe, sponge, brush, and the like. The composition may be applied while the skin is wet or dry, and may be wiped off the skin, rinsed off the skin, or the skin may be allowed to dry after application of the composition. It is particularly desired that the composition be applied to the skin via a pre-soaked wipe and is allowed to dry off the skin without further washing or cleaning by the user. The used wipe may be disposed of by the user. The invention described herein may be practice in the absence of any component, ingredient or step not specifically disclosed herein or may include additional components or steps that are not expressly disclosed herein.

As noted above, the present invention is directed to compositions that can be used to clean a variety of cosmetics off of the surface of a user's skin effectively and efficiently. The inventive compositions should be capable of removing, for example, foundation, mascara and lipstick efficiently. Further, the inventive compositions should be substantially free of silicones, if not entirely free of silicones. Also, the inventive compositions should include at least one dry emollient, and at least one oily emollient in combination with each other. Finally, it may be desirable, although not critical, that the composition include a lesser amount of cleansing components than that in previous methods. For example, previous methods include cleansing components in amounts of about 10-11%, and the present invention may include cleansing components in an amount of about 8-10% or about 8% by weight of the total composition.

The present invention may be better understood through the following examples, which are exemplary in nature and not intended to be limiting to any specific combination of elements. Examples 2-6 demonstrate that the compositions including a combination of dry and oily emollients in the amounts described above provide a suitable cleansing efficiency for three different cosmetics (mascara, lipstick, and foundation), while avoiding the use of silicones, and also avoiding the use of compositions including only a dry emollient or only an oily emollient.

As a result of the various tests conducted to show removal of foundation, mascara and lipstick, it can be seen that compositions including about 3:1 to about 1:1 percent of dry emollient to oily emollient provide safe, efficient, and useful cleansing composition, while avoiding the addition of silicone materials, avoiding the use of only dry emollients (which may irritate the user), and avoiding the use of only oily emollients (which provide a greasy or oily feel). Further, as seen in Example 6, a panel of individuals was asked to judge the feel of an inventive composition (3:1 ratio of dry emollient to oily emollient) as compared to components of a prior, silicone-containing example. The results demonstrate that the Composition 1 dried quicker and was less greasy/oily than the prior composition.

Therefore, the compositions including a combination of a dry emollient and oily emollient, particularly those in a ratio of 3:1 to 1:1 dry emollient to oily emollient are considered beneficial and useful as compared to other samples tested.

Example 1—Inventive Composition Compared to Commercially Available Cleaner

The following composition provides one embodiment (Silicone-Free Cleaner) of a useful cleaning composition, as compared to a commercially available skin cleaner (Silicone-Containing Cleaner).

| Component | Silicone-Free Cleaner | Silicone-Containing Cleaner |
|---|---|---|
| Water | Q.S. | Q.S. |
| Thickeners | 0.27 | 0.25 |
| Emulsifiers | 1.50 | 1.50 |
| Dicaprylyl Carbonate | 6.00 | — |
| Heptyl Undecylenate | 2.00 | — |
| Isostearyl Palmitate | — | 2.00 |
| Isononyl Isononanoate | — | 2.00 |
| Pentaerythrityl Tetraethylhexanoate | — | 2.00 |
| Cetyl Ethylhexanoate | — | 2.00 |
| Cyclopentasiloxane | — | 2.00 |
| Humectants | 2.00 | 1.00 |
| Preservatives | 1.00 | 0.88 |
| Fragrances | 0.25 | 0.06 |
| Excipients | 0.10 | 0.10 |
| Sodium Hydroxide | 0.09 | 0.08 |

As can be seen, the composition differs not only in the components but in the relative amounts of components. The silicone-free cleaner is one embodiment of a useful cleaner of the present invention, and as can be seen it is free of silicone containing materials, while the silicone-containing cleaner includes cyclopentasiloxane. In this example, there is a combination of a dry emollient (dicaprylyl carbonate) and an oily emollient (heptyl undecylenate) in a total amount of 8% by weight of the composition. The weight ratio of dicaprylyl carbonate to heptyl undecylenate is 3:1. Water is present in a sufficient quantity by weight of the composition. The inventive example provides a skin cleaning composition that is at least as effective as the silicone-containing cleaner for removal of mascara, lipstick and foundation, but is also substantially non-irritating to a user and does not leave a greasy or oily feeling on the skin after application.

Example 2—Compositions of Varying Ratios of Components

To demonstrate the ability of cleansers of the present invention to clean various cosmetics with a suitable cleansing efficiency, six cleansers were prepared, including a comparative prior art composition that includes silicone, as well as five compositions of varying ratios of cleansing components. Each of the cleansing compositions prepared in the present Example include cleaning components in amounts of about 10% by weight of the composition. Composition 1 includes a 3:1 ratio of dicaprylyl carbonate (DC) and heptyl undecylenate (HU) (7.5% DC, 2.5% HU). Composition 2 includes a 6:1 ratio of DC to HU. Composition 3 includes a 1:1 ratio of DC to HU. Composition 4 includes a 1:0 ratio of DC to HU, and thus Composition 4 is free of oily emollients, including only dry emollients in an amount of 10%. Composition 5 includes a 0:1 ratio of DC to HU, and thus composition 5 is free of dry emollients, and includes only oily emollients in an amount of about 10%.

Finally, Comparative 1 includes silicone, and noticeably is free of DC and HU, while Compositions 1-5 are free of silicone containing materials. Compositions 1-5 include a total weight percent of about 10% DC and HU combined. The compositions of the samples are described in the tables below.

| Component | Composition 1 (3:1 ratio) | Composition 2 (6:1 ratio) | Composition 3 (1:1 ratio) |
|---|---|---|---|
| Water | Q.S. | Q.S | Q.S |
| Thickeners | 0.25 | 0.25 | 0.25 |
| Emulsifiers | 1.50 | 1.50 | 1.50 |
| Dicaprylyl Carbonate | 7.50 | 8.57 | 5.00 |
| Heptyl Undecylenate | 2.50 | 1.43 | 5.00 |
| Humectants | 1.00 | 1.00 | 1.00 |
| Preservatives | 0.88 | 0.88 | 0.88 |
| Sodium Hydroxide | 0.016 | 0.016 | 0.016 |

| Component | Composition 4 (1:0 ratio) | Composition 5 (0:1 ratio) | Comparative 1 (silicone-containing) |
|---|---|---|---|
| Water | Q.S | Q.S | Q.S. |
| Thickeners | 0.25 | 0.25 | 0.25 |
| Emulsifiers | 1.50 | 1.50 | 1.50 |
| Dicaprylyl Carbonate | 10.0 | 0 | — |
| Heptyl Undecylenate | 0 | 10.0 | — |
| Isostearyl Palmitate | — | — | 2.00 |
| Isononyl Isononanoate | — | — | 2.00 |
| Pentaerythrityl Tetraethylhexanoate | — | — | 2.00 |
| Cetyl Ethylhexanoate | — | — | 2.00 |
| Cyclopentasiloxane | — | — | 2.00 |
| Humectants | 1.00 | 1.00 | 1.00 |
| Preservatives | 0.88 | 0.88 | 0.88 |
| Sodium Hydroxide | 0.016 | 0.016 | 0.016 |

Example 3—In Vitro Cleansing Efficiency

The compositions prepared above were tested for in vitro cleansing ability. Four runs were conducted for each composition. The tests were conducted using a HunterLab LabScan XE system to measure the removal of foundation (Revlon® Colorstay™450 Mocha) from un-hydrated Vitro-Skin® circular samples. The test methodology for each composition (Compositions 1-5, Comparative 1) was as follows:

1. Mark 2 circular test area of diameter 2.54 cm (1") on one sample of un-hydrated VITRO-SKIN®. Draw the circle with a compass or by tracing a circular object with a diameter 2.54 cm (1").
2. With a syringe, expel 0.01 g of foundation on to the middle of one circle.
3. With a gloved finger, spread the foundation on to the circle, staying within the line.
4. Repeat 2 & 3 on the other circle.
5. Air-Dry the sample for 20-30 minutes.
6. Place the sample in the VITRO-SKIN® hydration chamber allowed it to hydrate for 12-24 hours.
7. After hydration, take sample out read pure vitro skin color and color of two coated circulars on HunterLab LabScan XE
8. Tape the sample securely onto the Washability & Wear tester.

9. Coat nonwoven with cleansing lotion (weight ratio of lotion/nonwoven=3.7) and then fix coated wipe on testing sled.
10. Set cleansing cycle at 3 cycles and speed at 5 inch/second.
11. Fix testing sled on the tester, put 987 g extra weight on top of testing sled and start test.
12. Read sample on HunterLab LabScan XE The results are seen in the chart of FIG. 1. As can be seen, Composition 1, which includes a 3:1 ratio of DC:HU provided a significantly greater cleansing efficiency as compared to Comparative 1, and also provided better cleaning from Compositions 2-4. Composition 5 provided a greater cleansing result, but it is noted that Composition 5 is free of a "dry" emollient (DC), and only contains heptyl undecylenate. While this sample provided sufficient cleaning of the color from the sample, this sample leaves an oily and greasy feel to a user, and would therefore be less desirable to a user.

Based upon this test, it is seen that the Composition 1 provides suitable cleaning of foundation from the sample, while avoiding a greasy/oily feel, also limiting risk of irritation to a user, and further avoiding the use of added silicone materials.

Example 4—Arm Test of Cleansing—Mascara

The six samples described above were then tested by hand and on human skin for mascara removal. The mascara tested was Cover Girl LASH BLAST 24 HOUR. Each sample was tested one time and testing of the mascara removal was conducted by using a chromometer to evaluate the level of color removal, as well as by visually observing the resulting samples on the skin after cleaning. This test was conducted to demonstrate the removal of mascara from the skin. As noted above, the desired cleanser is capable of removing foundation, mascara and lipstick efficiently and without leaving greasy/oily residue and while avoiding the use of added silicone materials.

To achieve this test, a circle template was applied to volar forearm and 2 circles in a row were drawn for six test sites. Each site on arm was measured with a HunterLab LabScan XE colorimeter to establish a baseline. Mascara (Cover Girl LASH BLAST 24 HOUR) was then applied to six sites and spread evenly with a gloved fingertip. Makeup was allowed to dry on arm for ~30 minutes. Photographs were taken of the test sites. Test sites were again measured with a HunterLab LabScan XE colorimeter.

Wipes were prepared by applying 3.7 grams of each of the six test products per 1 gram of wipe. For Compositions 1-4 and Comparative 1, each test site was swiped five times with a wipe containing the test product. Note that Composition 5 was not tested with only five swipes. After the five swipes, photographs were again taken of the test sites and the test sites were again measured with a HunterLab LabScan XE colorimeter.

Each test site was then swiped five more times with wipe containing the test product (giving a total of ten swipes). Photographs were again taken of the test sites and the test sites were again measured with a HunterLab LabScan XE colorimeter.

Figure 2:
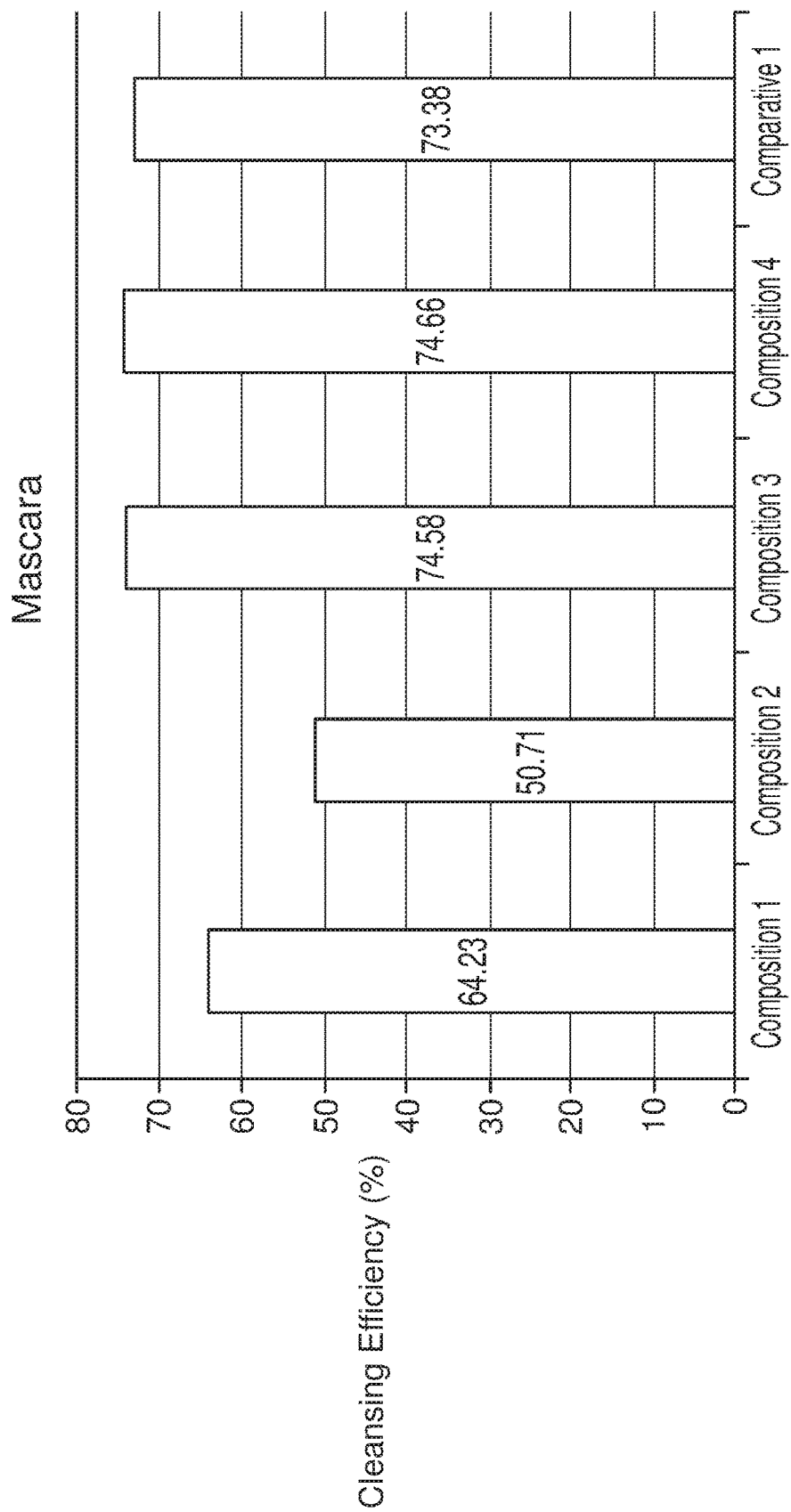
FIG. 2 is a chart summarizing the test data for five cycles in Example 4.
Figure 3:
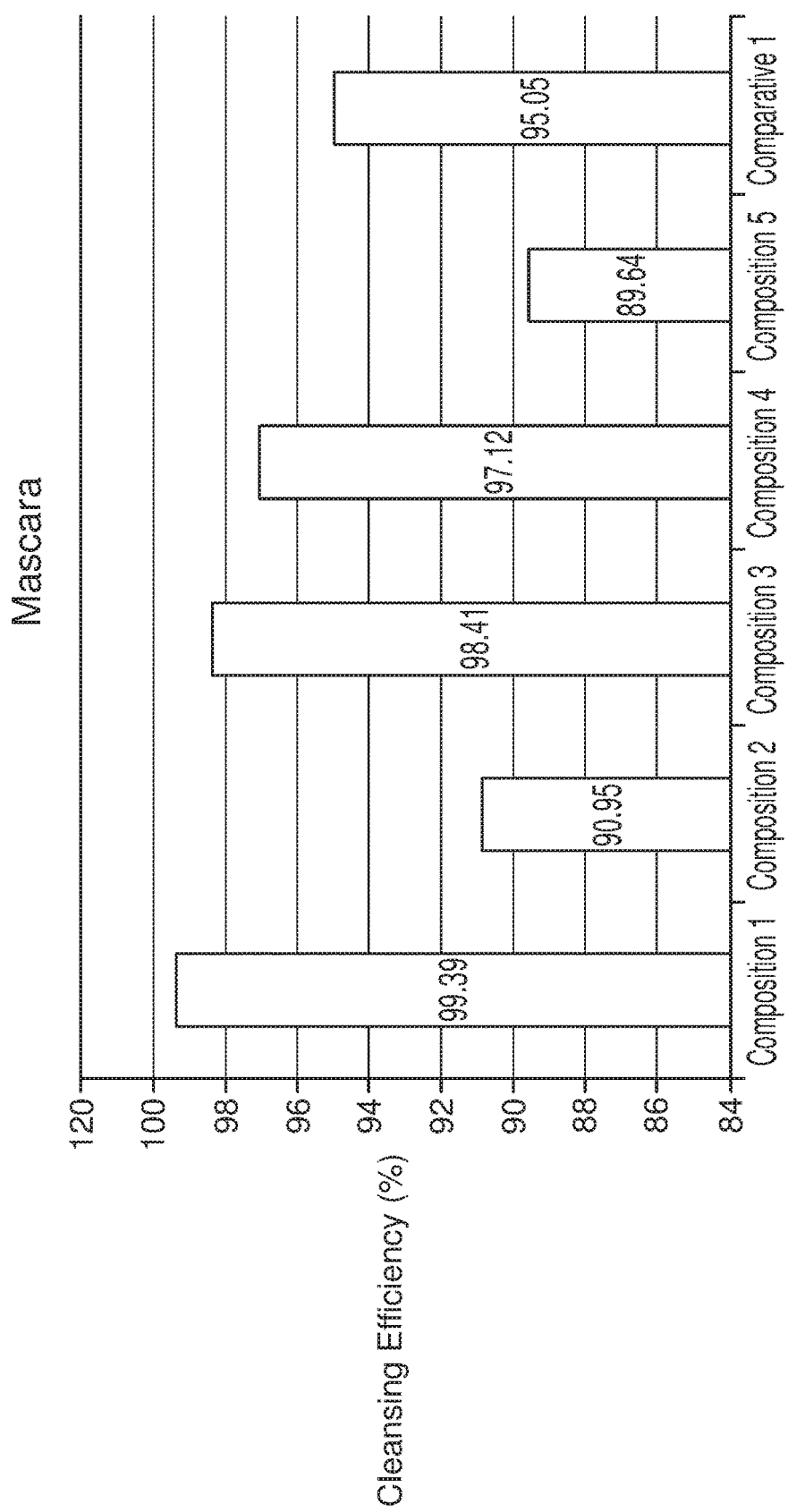
FIG. 3 is a chart summarizing the test data for ten cycles in Example 4.

Results after 5 cycles can be seen in FIG. 2, and the results after 10 cycles can be seen in FIG. 3. As can be seen, after five cycles, the cleansing efficiency for compositions 1, 3, and 4 were comparable to that of the comparative sample. However, after 10 cycles, it can be seen that Compositions 1, 3 and 4 provide a greater cleansing efficiency of the mascara from the skin to that of a comparative sample. The resulting skin was also viewed visually by an observer, and it was noted that composition 5 and composition 1 visually appeared to sufficiently clean mascara the best after 5 and 10 swipes, respectively, while composition 3 and composition 2 did not visually appear to suitably clean the mascara from the skin after 5 swipes and 10 swipes, respectively.

The results of this test showed that the inventive composition provides suitable and efficient removal of mascara compared to the prior composition and a composition that is free of dry emollients. Although composition 4 was suitable in cleaning, it is again noted that this composition is free of oily emollients, and may risk irritating the skin of the user.

Example 5—Arm Test of Cleansing—Lipstick

The six samples described above were then tested by hand and on human skin for lipstick removal. The lipstick tested was Cover Girl OUTLAST All Day Lip Color. Each sample was tested one time and testing of the lipstick removal was conducted by using a chromometer to evaluate the level of color removal, as well as by visually observing the resulting samples on the skin after cleaning. This test was conducted to demonstrate the removal of lipstick from the skin. As noted above, the desired cleanser is capable of removing foundation, mascara and lipstick efficiently and without leaving greasy/oily residue, without risking irritation to the user, and while avoiding the use of added silicone materials.

The test methodology used in Example 4 was repeated substituting the mascara for Cover Girl OUTLAST All Day Lip Color in each of the six test sites. The same products were tested and measured after five swipes for Compositions 1-4 and Comparative 1, and ten swipes for all compositions.

Figure 4:
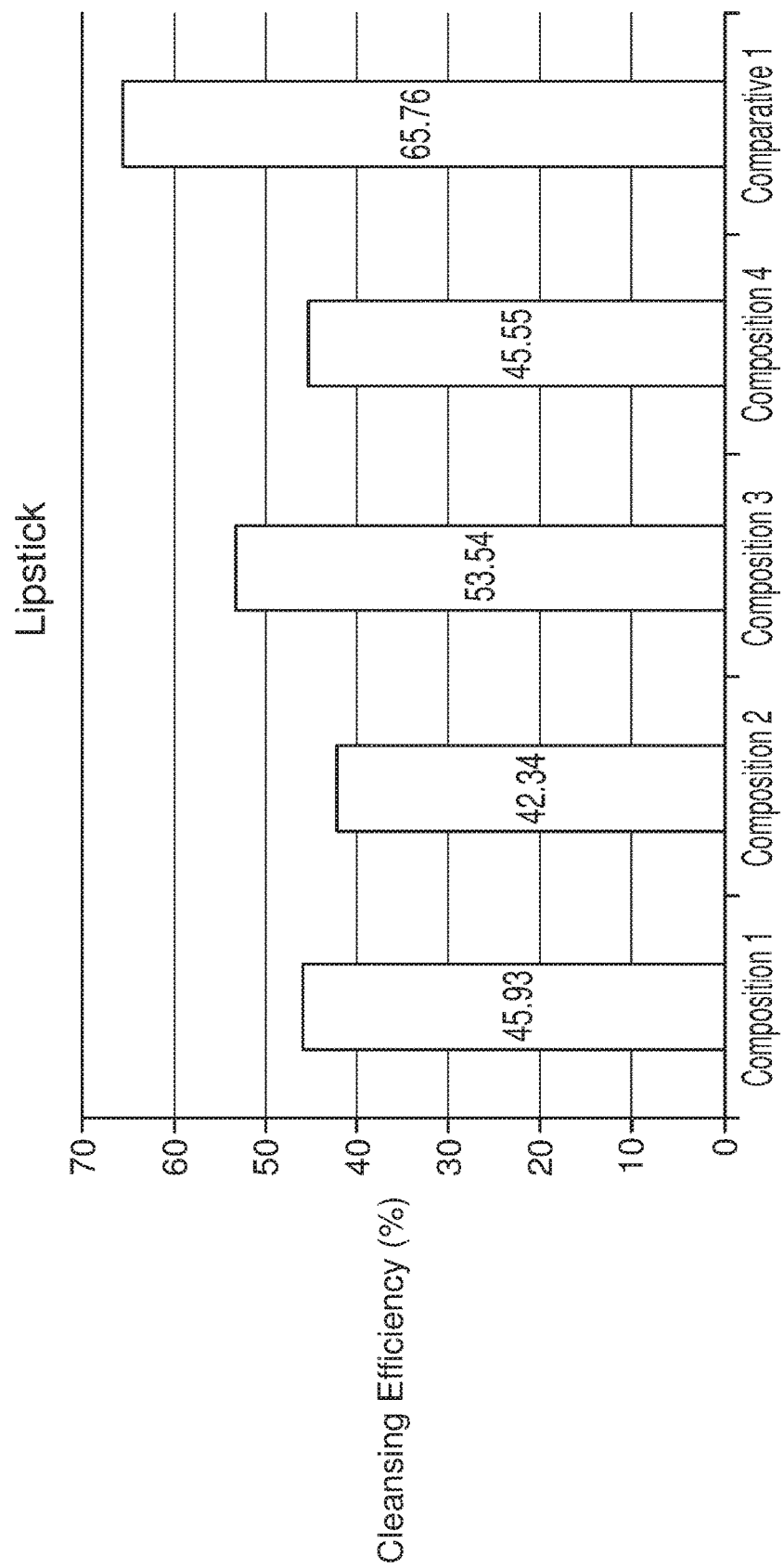
FIG. 4 is a chart summarizing the test data for five cycles in Example 5.

Results after 5 cycles can be seen in FIG. 4, and the results after 10 cycles can be seen in FIG. 5. As can be seen, after five cycles, the comparative 1 sample had the greatest cleansing efficiency. However, after 10 cycles, it can be seen that each of the compositions 1-5 provided at least 80% cleansing efficiency. The resulting skin was also viewed visually by an observer, and it was noted that composition 5 and composition 1 visually appeared to sufficiently clean lipstick the best after 5 swipes and 10 swipes, respectively, while composition 4 and composition 5 did not visually appear to suitably clean the lipstick from the skin after 5 swipes and after 10 swipes, respectively.

The results of this test showed that the inventive compositions provide suitable removal of lipstick compared to other sample compositions, including the previous silicone-containing composition. The lipstick removal for the compositions is not as high as a silicone-containing composition, but provides a suitable cleansing efficiency while avoiding inclusion of silicone materials.

Example 6: Drying Test of Cleansing Formulations

| Component | Cleanser Composition 1 (% weight) | Cleanser Composition 2 (% weight) |
|---|---|---|
| Isostearyl Palmitate | — | 20 |
| Isononyl Isononanoate | — | 20 |
| Pentaerythrityl Tetraethylhexanoate | — | 20 |
| Cetyl Ethylhexanoate | — | 20 |
| Cyclopentasiloxane | — | 20 |

-continued

| Component | Cleanser Composition 1 (% weight) | Cleanser Composition 2 (% weight) |
|---|---|---|
| Dicaprylyl Carbonate | 75 | |
| Heptyl Undecylenate | 25 | |
| Total | 100 | 100 |

The two cleanser compositions described above were prepared and tested on human skin for drying speed. A drop of each formulation was applied on the skin of four individuals, then rubbed to be absorbed by each individual. It was observed that Cleaner Composition 2, which contains multiple oily components, left an oily/greasy feel, while the Cleanser Composition 1 was less oily, leaving a pleasant feel on the skin. Cleanser composition 1 is believed to exhibit a comparable cleansing efficacy to Cleanser Composition 2 without the unpleasant greasiness.

What is claimed is:

1. A personal care composition comprising:
    (a) a hydrophilic phase comprising water, the hydrophilic phase being present in an amount of from about 85% to about 90% by weight of the personal care composition;
    (b) a lipophilic phase comprising a dry emollient and an oily emollient, the dry emollient being present in a greater amount by weight than the oily emollient, and the dry emollient and oily emollient being present in a ratio of from about 3:1 to about 1:1 by weight, wherein the dry emollient comprises a carbonate ester selected from the group consisting of dicaprylyl carbonate, cetyl carbonate, cetearyl carbonate, stearyl carbonate, C12-C15 alkyl carbonate and combinations thereof, and wherein the oily emollient comprises an ester selected from the group consisting of heptyl undecylenate, tridecyl neopentanoate, isostearyl palmitate, cetyl ricinoleate, cetyl octanoate, isononyl isononanoate, butyl stearate, octyldodecyl soyate, tridecyl erucate, octyldodecyl erucate/eicosil erucate, diisopropyl adipate, dioctyl sebacate, dioctyl succinate, dioctyl maleate, diisostearyl adipate, diethyl sebacate and combinations thereof;
    wherein the personal care composition is free of silicone or silicone containing materials.

2. The personal care composition of claim 1, wherein said dry emollient and oily emollient are present in a weight ratio of about 3:1.

3. The personal care composition of claim 1, wherein the personal care composition further comprises a humectant and an emulsifier.

4. The personal care composition of claim 1, wherein the personal care composition further comprises a preservative.

5. The personal care composition of claim 1, wherein the personal care composition further comprises a fragrance.

6. The personal care composition of claim 1, wherein the personal care composition further comprises a neutralizer.

7. The personal care composition of claim 1, wherein the personal care composition is a cleansing composition.

8. The personal care composition of claim 1, wherein the composition is a substantially non-irritating cleansing composition.

9. A method of cleaning the skin of a user without irritating skin, comprising the step of:
    (a) applying a personal care composition to the skin of a user, the composition comprising:
        (i) a hydrophilic phase comprising water, the hydrophilic phase being present in an amount of from about 85% to about 90% by weight of the personal care composition;
        (ii) a lipophilic phase comprising a dry emollient and an oily emollient, the dry emollient being present in a greater amount by weight than the oily emollient, and the dry emollient and oily emollient being present in a ratio of from about 3:1 to about 1:1 by weight, wherein the dry emollient comprises a carbonate ester selected from the group consisting of dicaprylyl carbonate, cetyl carbonate, cetearyl carbonate, stearyl carbonate, C12-C15 alkyl carbonate and combinations thereof, and wherein the oily emollient comprises an ester selected from the group consisting of heptyl undecylenate, tridecyl neopentanoate, isostearyl palmitate, cetyl ricinoleate, cetyl octanoate, isononyl isononanoate, butyl stearate, octyldodecyl soyate, tridecyl erucate, octyldodecyl erucate/eicosil erucate, diisopropyl adipate, dioctyl sebacate, dioctyl succinate, dioctyl maleate, diisostearyl adipate, diethyl sebacate and combinations thereof;
        wherein the personal care composition is free of silicone or silicone containing materials; and
    (b) one of rinsing the composition off the skin, leaving the composition to dry on the skin, or wiping the composition off the skin.

10. The method of claim 9, wherein said step of applying comprises applying by a wipe, sheet, sponge, or brush.

11. The method of claim 9, wherein said step of applying comprises applying by hand.

12. The method of claim 9, wherein said dry emollient and oily emollient are present in a weight ratio of about 3:1.

13. The method of claim 9, wherein the composition further comprises a humectant and an emulsifier.

14. The method of claim 9, wherein the composition further comprises a preservative.

15. The method of claim 9, wherein the composition further comprises a fragrance.

16. The method of claim 9, wherein the composition further comprises a neutralizer.

17. The method of claim 9, wherein the composition is a cleansing composition.

18. The method of claim 9, wherein the composition is a substantially non-irritating cleansing composition.

* * * * *